(12) United States Patent
Schillizzi et al.

(10) Patent No.: US 8,172,743 B2
(45) Date of Patent: *May 8, 2012

(54) INTERACTIVE HYPNOTIC BIO-STABILIZATION SYSTEM

(76) Inventors: Dominick Schillizzi, Rego Park, NY (US); Beauregard Robinson, Brooklyn, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/962,884

(22) Filed: Dec. 8, 2010

(65) Prior Publication Data

US 2011/0077454 A1    Mar. 31, 2011

Related U.S. Application Data

(63) Continuation of application No. 11/212,852, filed on Aug. 26, 2005, now Pat. No. 7,850,597.

(51) Int. Cl.
*A61M 21/00*    (2006.01)

(52) U.S. Cl. ............... 600/27; 600/26; 600/28; 128/897

(58) Field of Classification Search .............. 600/21–22, 600/26–28; 128/897, 898
See application file for complete search history.

(56) References Cited

U.S. PATENT DOCUMENTS

| | | | |
|---|---|---|---|
| 4,215,680 A | 8/1980 | Okuda | |
| 4,710,655 A | 12/1987 | Masaki | |
| 5,159,640 A | 10/1992 | Bick | |
| 5,219,322 A | 6/1993 | Weathers | |
| 5,266,070 A | 11/1993 | Hagiwara et al. | |
| 5,425,699 A | 6/1995 | Speigel | |
| 5,694,939 A | 12/1997 | Cowings | |
| 7,850,597 B2 | 12/2010 | Schillizzi et al. | |
| 2004/0244807 A1 | 12/2004 | Sun et al. | |
| 2005/0075532 A1 | 4/2005 | Lee et al. | |

FOREIGN PATENT DOCUMENTS

| | | |
|---|---|---|
| DE | 91 07 576 U1 | 1/1992 |
| EP | 0 431 793 A2 | 6/1991 |
| EP | 0 872 255 A1 | 10/1998 |
| WO | WO 02/094099 A1 | 11/2002 |

*Primary Examiner* — Charles A Marmor, II
*Assistant Examiner* — Carrie R Dorna
(74) *Attorney, Agent, or Firm* — Carter, DeLuca, Farrell & Schmidt, LLP

(57) ABSTRACT

An interactive biological stabilization (IBS) device includes at least one communication path enabling operative coupling with at least one patient data monitoring device, and a processing device enabled for operative coupling with the at least one patient monitoring device through the at least one communication path. The processing device includes a hypnotherapeutic treatment decision block selecting at least one hypnotherapeutic treatment modality based on patient data received from the at least one patient data monitoring device through the at least one communication path. A system for interactively biologically stabilizing a patient includes the IBS device. A method for interactively biologically stabilizing a patient includes the steps of providing at least one apparatus monitoring vital patient data and providing at least one processor processing the vital patient data which selects a hypnotherapeutic treatment modality based on the processing of the vital patient data.

20 Claims, 5 Drawing Sheets

INTERACTIVE HYPNOTIC BIO-STABILIZATION SYSTEM

CROSS-REFERENCE TO RELATED APPLICATIONS

This application claims priority to U.S. patent application Ser. No. 11/212,852 by D. Schillizzi et al. entitled "INTERACTIVE BIO-STABILIZATION SYSTEM", filed on Aug. 26, 2005, now U.S. Patent Application Publication No. 2007/0049805 A1, entitled "INTERACTIVE BIO-STABILIZATION SYSTEM", published on Mar. 1, 2007, the entire contents of which is incorporated herein by reference.

BRIEF DESCRIPTION OF THE DRAWINGS

The subject matter regarded as the embodiments is particularly pointed out and distinctly claimed in the concluding portion of the specification. The embodiments, however, both as to organization and method of operation, together with objects, features, and advantages thereof, may best be understood by reference to the following detailed description when read with the accompanying drawings in which:

DETAILED DESCRIPTION

The present disclosure will be understood more fully from the detailed description given below and from the accompanying drawings of particular embodiments of the invention which, however, should not be taken to limit the invention to a specific embodiment but are for explanatory purposes.

Numerous specific details may be set forth herein to provide a thorough understanding of a number of possible embodiments of an interactive biological stabilization system incorporating the present disclosure. It will be understood by those skilled in the art, however, that the embodiments may be practiced without these specific details. In other instances, well-known methods, procedures, components and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments disclosed herein are not necessarily limited in this context.

It is worthy to note that any reference in the specification to "one embodiment" or "an embodiment" means that a particular feature, structure, or characteristic described in connection with the embodiment is included in at least one embodiment. The appearances of the phrase "in one embodiment" in various places in the specification are not necessarily all referring to the same embodiment.

Figure 1:
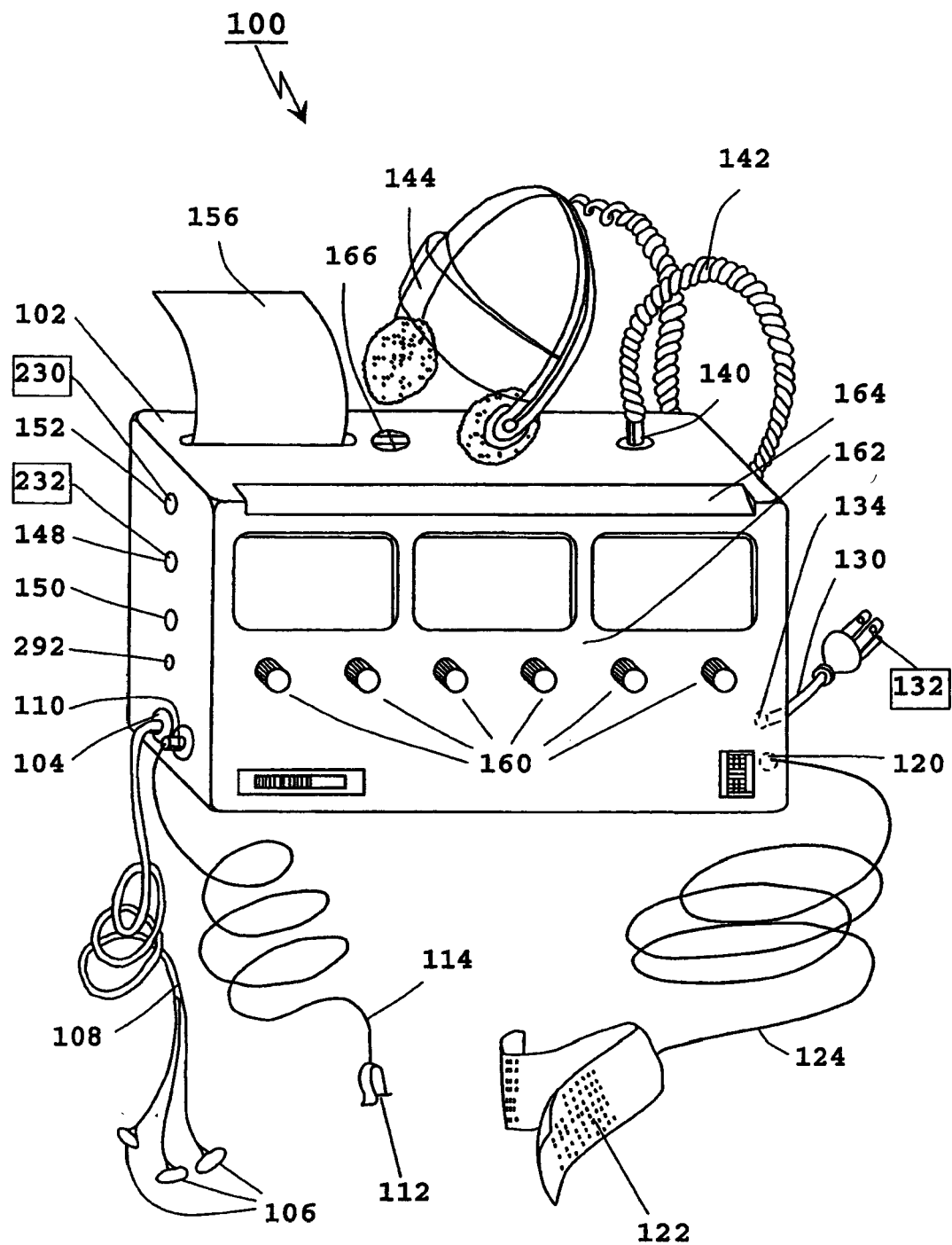
FIG. 1 is a perspective view of an interactive biological stabilization system according to the present disclosure.
Figure 2:
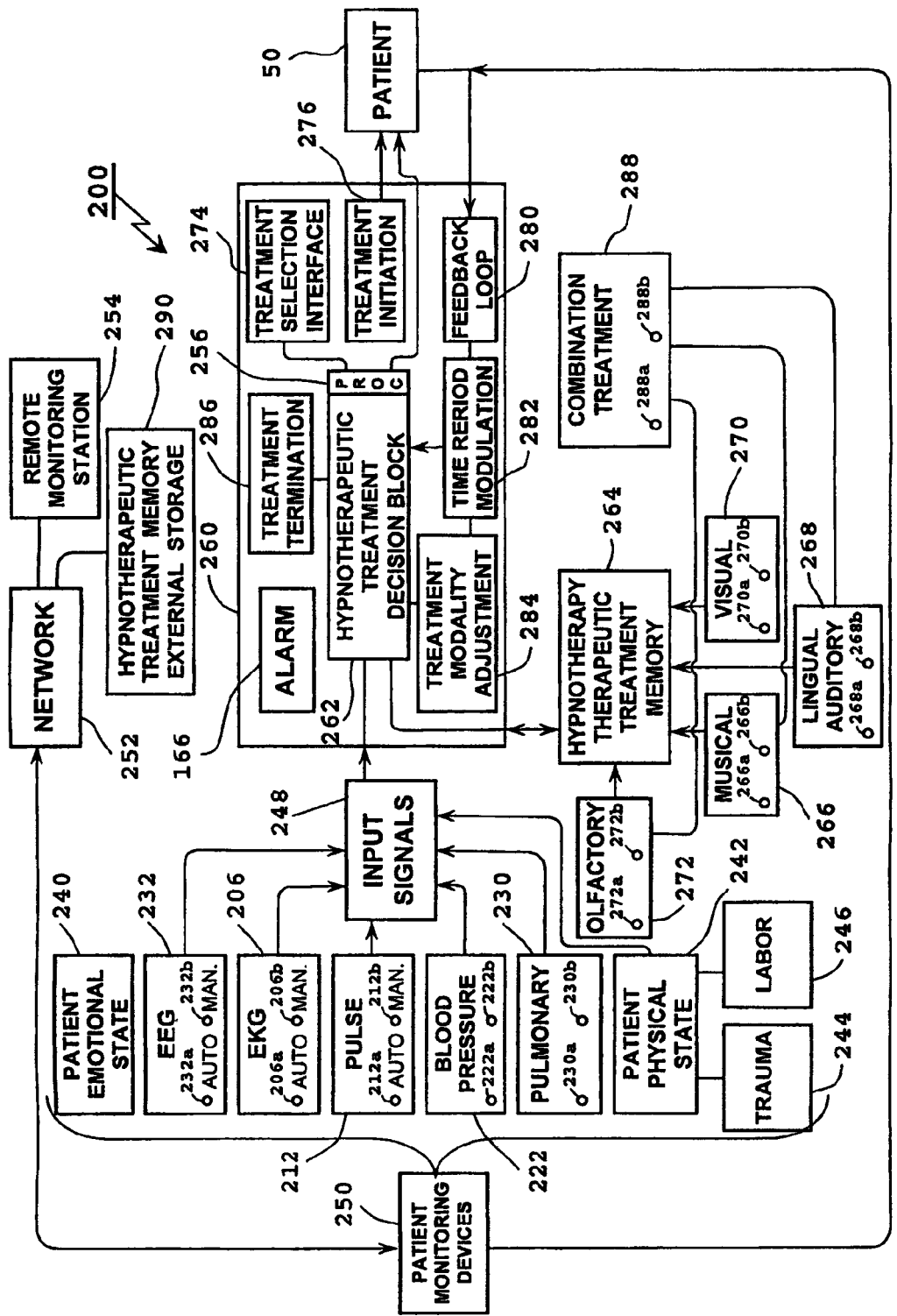
FIG. 2 is a block diagram of the interactive biological stabilization system of FIG. 1.

Turning now to the details of the present disclosure, FIG. 1 shows a perspective view of an interactive biological stabilization (IBS) device 100 according to the present disclosure. FIG. 2 shows a block diagram of an IBS system 200 which includes the IBS device 100. More particularly, the IBS device 100 includes a housing 102 which protects and integrates the components of the IBS device 100. The housing 102 includes at least one communication path, such as port 104 for cardiac electrodes 106 and coupled lead wires 108 which enable operative coupling with at least one patient data monitoring device 250 such as cardiac monitor 206 which provides electrocardiogram (EKG) output.

Other communication paths may include, but are not limited to, port 110 for pulse monitor sensor 112 and coupled lead wire 114 which enable operative coupling to patient pulse monitoring device 212; and port 120 for blood pressure cuff 122 and coupled lead wire 124 which enable operative coupling to patient blood pressure monitoring device 212. The communication paths may be hard wired or wireless.

Other patient monitoring devices 250 may include, but are not limited to, pulmonary monitoring device 230 which provides respiratory data through communication port 148 and cerebral monitor 232 which provides electroencephalogram (EEG) monitoring data through communication port 152.

Patient monitoring devices 250 may include manual monitoring of the patient emotional state 240 and manual monitoring of the patient physical state 242. The manual monitoring of the patient emotional state 240 includes capability of manual initiation of an appropriate hypnotherapeutic treatment modality for indications such as hysteria (which may also be considered a physical state).

The patient physical state may include trauma 244 or labor 246. The trauma 244 may include unconsciousness and the labor 246 includes both birth delivery and post-natal conditions. The manual monitoring of the patient physical state 242 includes capability of manual initiation of an appropriate hypnotherapeutic treatment modality for the particular physical state being experienced by the patient.

The patient monitoring devices 250 may be coupled to a network 252 through a remote monitoring port 150 in the housing 102. The network 252 may be a local area network (LAN) internal to a medical facility or office or an external network, such as the internet. The network 252 then couples the patient monitoring devices 250 to a remote monitoring station 254.

Typically, the patient monitoring devices 250 provide input signals 248 to a processing device 260 enabled for operative coupling with the at least one patient monitoring device 250 through the at least one communication path which include ports 104, 110, 120, 148, and 152.

The processing device 260 includes a hypnotherapeutic treatment decision block 262 which selects at least one hypnotherapeutic treatment modality based on vital patient data received from the at least one patient data monitoring device 250 through the at least one communication path. The hypnotherapeutic treatment decision block 262 includes at least one processor 256 and/or an application specific integrated circuit (ASIC) for executing a set of stored instructions for performing functions described herein. The set of instructions may be stored on a computer readable medium, such as a CD-ROM, and downloaded to the hypnotherapeutic treatment decision block 262.

The hypnotherapeutic treatment modalities may include a musical treatment 266, an auditory or lingual treatment 268, a visual treatment 270 or an olfactory treatment 272, at least one of which is stored in a hypnotherapy therapeutic treatment memory 264. The olfactory treatment 272 may include various aromatherapies. That is, the hypnotherapeutic treatment memory 264 stores therapeutic indications for at least one hypnotherapeutic treatment modality. The hypnotherapeutic treatment modalities may include a combination treatment 288 of two or more treatments selected from the group consisting of musical treatment 266, auditory or lingual treatment 268, visual treatment 270, and olfactory treatment 272.

The hypnotherapeutic treatment memory 264 is operatively coupled to the treatment decision block 262. A hypnotherapeutic treatment selection interface 274 is operatively coupled to the hypnotherapeutic treatment decision block 262 and, based on a signal from the decision block 262, selects the appropriate hypnotherapeutic treatment modality from the memory 264.

Figure 3:
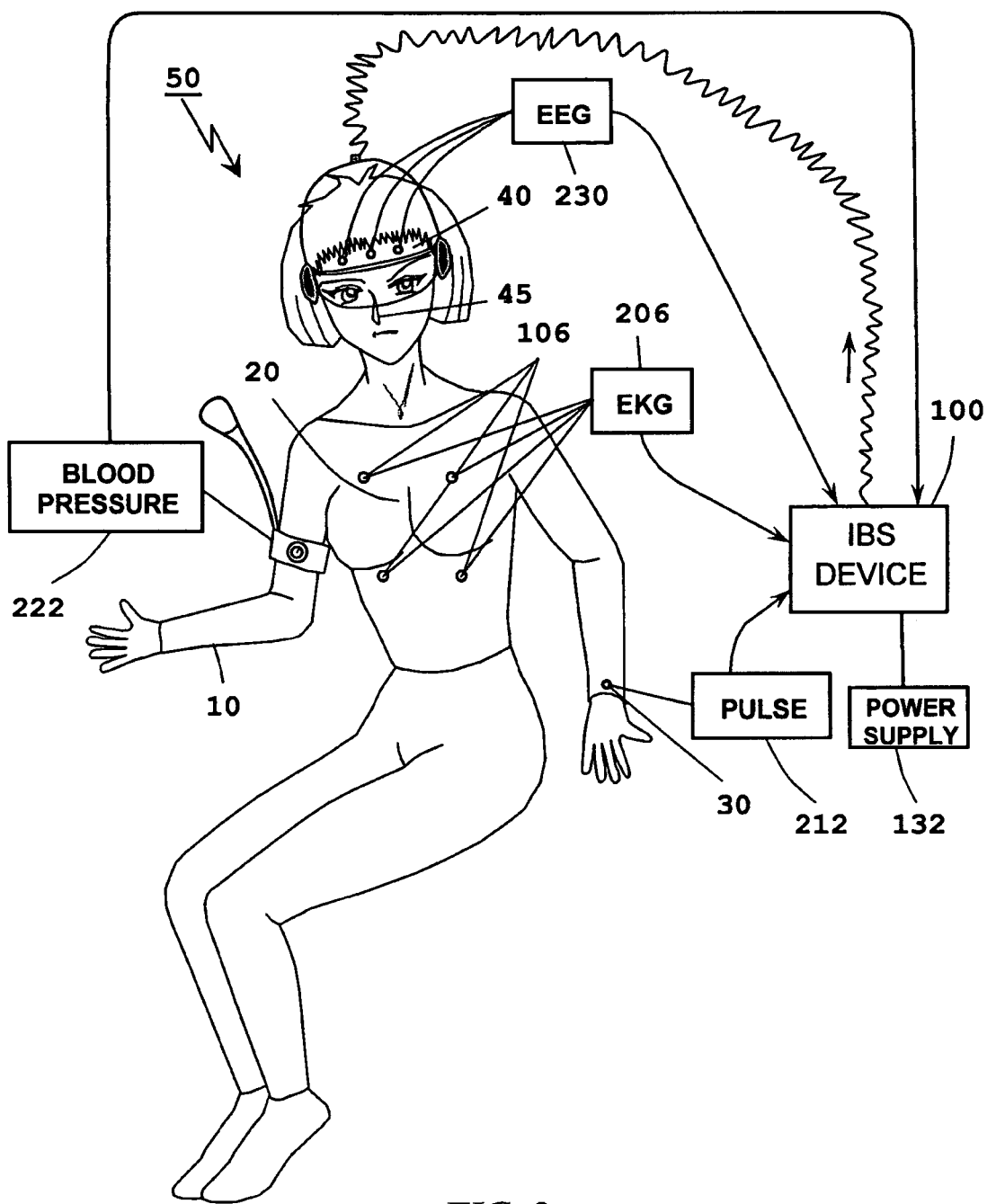
FIG. 3 illustrates a patient receiving biological stabilization treatment according to the present disclosure.

A treatment initiation circuit 276 is operatively coupled to the treatment selection interface 274 and initiates the at least one selected hypnotherapeutic treatment to a patient 50 (See FIG. 3). The selected hypnotherapeutic treatment is provided to the patient 50 through a port 140 in the housing 102. Lead wire 142 is coupled to the treatment initiation circuit 276 and serves as a communication path from the processor 262 to a headset 144.

The headset 144 may be either an auditory headset or a combined audio-visual headset. The headset 144 provides the patient 200 directly, as appropriate with the type of headset, with the auditory or lingual, musical and visual treatment modalities 266, 268 and 270. The auditory treatment 268 may include, for example and is not limited to, sounds of nature such as rushing water or ocean waves or of wildlife. In one embodiment, the headset 144 may be configured to provide the patient 50 with the olfactory treatment 272 to the patient's nose 45 (See FIG. 3).

The processing device 260 may further include a feedback loop 280 which is operatively coupled to the at least one patient monitoring device 250 and receives patient data through the at least one communication path 104, 110, 120, 148, 152 and is operatively coupled to the treatment decision block 262. A time period modulation block 282 is operatively coupled to the feedback loop 280 and to the treatment decision block 262. The time period modulation block 282 adjusts the time period for applying the at least one selected hypnotherapeutic treatment modality to the patient 50 upon receiving a signal from the treatment decision block 262.

In addition, a treatment modality adjustment block 284 may be operatively coupled to the feedback loop 280 and to the treatment decision block 262. The treatment modality adjustment block 284 selects at least another one of the at least one hypnotherapeutic treatment modalities 266, 268, 270 or 272 from the therapeutic treatment memory 264 upon receiving a signal from the treatment decision block 262.

The processing device 260 may further include a treatment termination block 286 which is operatively coupled to the treatment decision block 262. The treatment termination block 286 terminates the at least one selected hypnotherapeutic treatment modality 266, 268, 270 or 272 upon receiving a signal from the treatment decision block 262.

Control switches 160 may be disposed typically in a front portion 162 of the housing 102 to control the various patient monitoring devices 250. The control switches 160 may be specifically configured to enable automatic monitoring and manual annunciation that the patient requires a particular hypnotherapeutic treatment modality, based on the patient vital signs or symptoms.

More particularly, the control switches 160 may be configured or combined with automatic monitoring switch 206a and manual control and annunciation switch 206b of cardiac monitor 206. When the automatic monitoring switch 206a is activated, the hypnotherapeutic treatment appropriate for a cardiac condition is only initiated by the treatment decision block 262 and processor 256 when the patient vital signs indicate cardiac distress. However, a user of the IBS device 100 may initiate manual control and annunciation switch 206b based on observation that the patient is in cardiac distress. The manual switch 206b directly signals the treatment decision block 262 and processor 256 to provide the hypnotherapeutic treatment appropriate for a cardiac condition.

Similarly, the control switches 160 may be configured or coordinated with automatic monitoring switch 212a and manual control and annunciation switch 212b of pulse monitor 212. When the automatic monitoring switch 212a is activated, the hypnotherapeutic treatment appropriate for a low, irregular or high pulse rate condition is only initiated by the treatment decision block 262 and processor 256 when the patient vital signs indicate pulse rate distress. However, a user of the IBS device 100 may initiate manual control and annunciation switch 212b based on observation that the patient is in pulse rate distress. The manual switch 212b directly signals the treatment decision block 262 and processor 256 to provide the hypnotherapeutic treatment appropriate for an abnormal pulse rate condition.

The control switches 160 may be configured or coordinated with automatic monitoring switch 222a and manual control and annunciation switch 222b of blood pressure monitor 222. When the automatic monitoring switch 222a is activated, the hypnotherapeutic treatment appropriate for a hypertension condition is only initiated by the treatment decision block 262 and processor 256 when the patient vital signs indicate hypertension. However, a user of the IBS device 100 may initiate manual control and annunciation switch 222b based on observation that the patient is experiencing hypertension. The manual switch 222b directly signals the treatment decision block 262 and processor 256 to provide the hypnotherapeutic treatment appropriate for a hypertension condition.

It can be recognized that in a similar manner, automatic monitoring switch 230a and manual control and annunciation switch 230b of pulmonary monitor 230, and automatic monitoring switch 232a and manual control and annunciation switch 232b of cerebral monitor 230 interact with the treatment decision block 262 and processor 256 when the patient vital signs indicate pulmonary distress such as asthma or emphysema or other pulmonary condition, or the vital signs indicate a cerebral dysfunction.

In an analogous manner, control switches 160 may be disposed typically in the front portion 162 of the housing 102 to control the various hypnotherapeutic treatment modalities. More particularly, the control switches 160 may be specifically configured to enable either automatic or manual initiation, control or termination of a particular hypnotherapeutic treatment modality. Musical treatment block 266 includes automatic control switch 266a and manual control switch 266b. Lingual or auditory treatment block 268 includes automatic control switch 268a and manual control switch 268b. Similarly, visual treatment block 270 includes automatic control switch 270a and manual control switch 270b, olfactory treatment block 272 includes automatic control switch 272a and manual control switch 272b, while combination treatment block 288 includes automatic control switch 288a and manual control switch 288b.

Electrical power is supplied to the IBS device 100 for operation of the various internal components within the housing 102 via a power supply 132 coupled to a power supply cord 130.

The IBS device 100 may include an EKG rhythm strip output printer 156 disposed in the housing 102. In addition, the IBS device may include either in addition to, or in lieu of, the EKG rhythm printer 156, an internal screen display 164 formed within the housing 102. The screen display 164 may be a touch screen for controlling the various functions and devices of the IBS device 100, such as the patient monitoring devices 250 or the hypnotherapeutic treatment modalities 266, 268, 270 or 272 and also for displaying the patient vital data.

Alternatively, the IBS device 100 may be coupled to an external screen display device (not shown). Additionally, an alarm 166 which may be both visual and audio is provided on the housing 102. The alarm 166 is operatively coupled to the treatment decision block 262 and annunciates if the patient vital signs monitored by the patient monitoring devices 250 indicate an abnormal or emergency condition.

In one embodiment, the IBS device 100 may exclude the patient monitoring devices 250 from enclosure within the housing 102. That is, the patient monitoring devices 250 may be external to the housing 102 (See FIG. 3 discussed below). The housing 102 may then include the processing device 260 and the associated blocks previously described above.

In another embodiment, referring to FIGS. 2 and 3, the present disclosure relates to an interactive biological stabilization (IBS) system 200. More particularly, the IBS system 200 includes at least one patient data monitoring device 250 and the processing device 260 operatively coupled with the at least one patient monitoring device 250 through at least one communication path 104, 110, 120, 148 or 152.

The patient monitoring device(s) 250 provide input signals 256 to the processing device 260. The processing device 260 includes at least the hypnotherapeutic treatment decision block 262 for selecting at least one hypnotherapeutic treatment modality based on vital patient data received from the at least one patient data monitoring device 250 through the at least one communication path 104, 110, 120, 148 or 152.

The hypnotherapeutic treatment selection interface 274 is operatively coupled to the hypnotherapeutic treatment decision block 262 and, based on a signal from the decision block 262, selects the appropriate hypnotherapeutic treatment modality from the memory 264. The treatment initiation circuit 276 is operatively coupled to the treatment selection interface 274 and initiates the at least one selected hypnotherapeutic treatment to the patient 50. One of ordinary skill in the art will recognize that the system 200 includes the processing device 260 and the associated blocks previously described above.

FIG. 3 illustrates patient 50 coupled to the various patient monitoring devices 250 of the IBS device 100 which functions as part of the system 200. More particularly, the patient monitoring devices 250, which include the blood pressure device 222 coupled around an arm 10 of the patient 50, cardiac electrodes 106 of EKG monitor 206 coupled to various locations on the chest 20 of the patient 50, the pulse monitor device 212 coupled to a wrist 30 of the patient 50, and the EEG monitor 230 coupled to the head 40 of the patient 50, are integrated with the IBS device 100.

The patient 50 is shown wearing the audio-visual headset 144 on the head 40. The patient monitoring devices 250 are illustrated in this example as being external to the IBS device 100 but are typically integrated into the IBS device 100 as previously discussed above.

In one embodiment, as shown in FIG. 2, the hypnotherapy treatment memory 264 is stored on an external storage device 290 and linked to the processing device 260 through network 252.

The hypnotherapy treatment memory files 264 may be stored in an analog, digital or other suitable format. For example, the musical treatments 266 may be stored in MP3 format while the auditory files 268 and visual files 270 may be stored in JPEG or streaming audio-visual format for later playback. The embodiments are not limited in this context.

In one embodiment, as shown in FIG. 1, the IBS device 100 includes a universal serial bus (USB) port 292 to enable downloading of the hypnotherapy treatment memory files 264 from a website on the network 252 or from a personal computer or an external server device.

Figure 4:
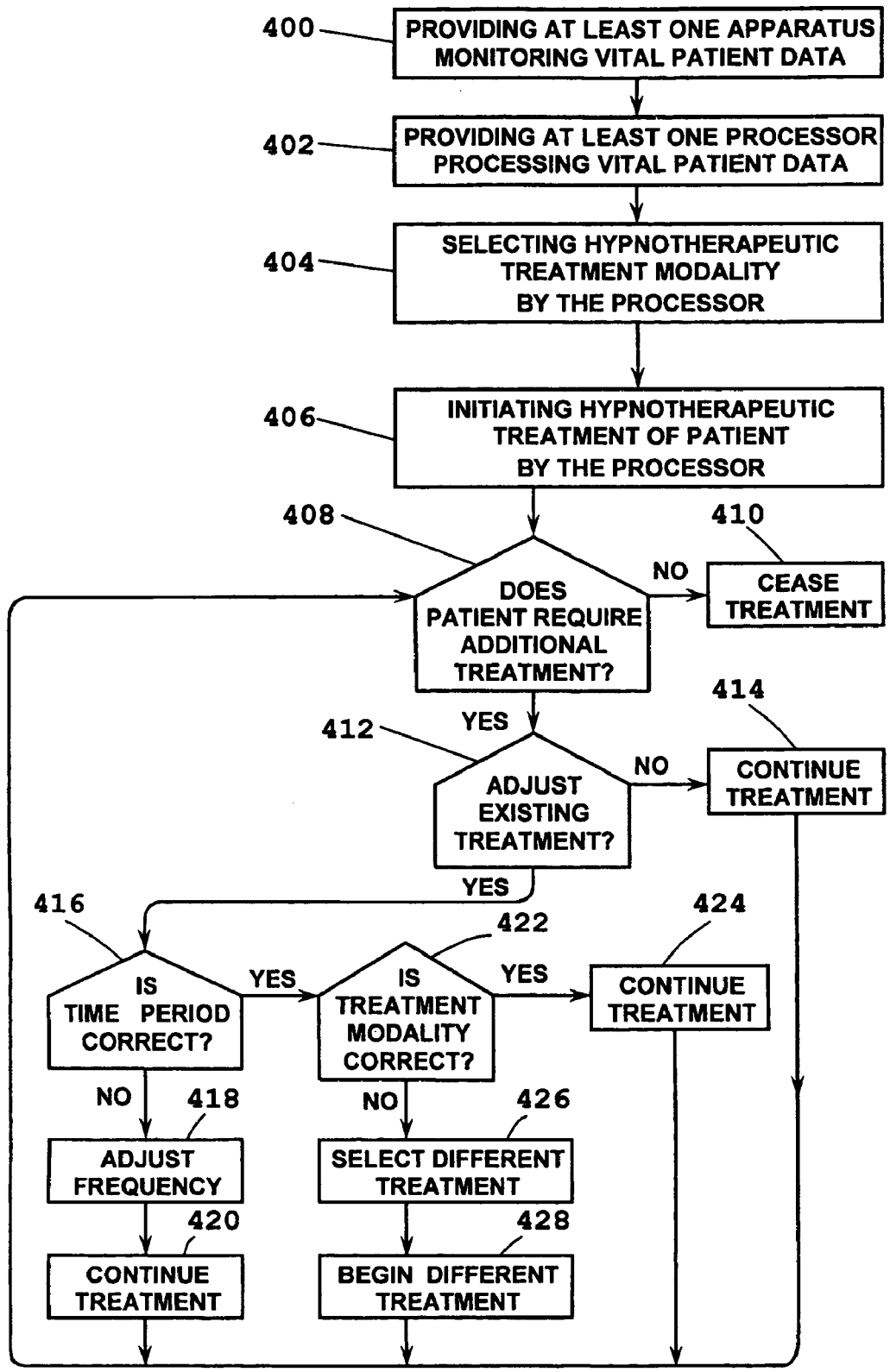
FIG. 4 illustrates a flow chart of a method of interactive biological stabilization according to the present disclosure.

Referring to FIG. 4, there is shown a flow chart illustrating an exemplary method for interactively biologically stabilizing a patient 50 in accordance with the present disclosure. The method includes Step 400 of providing at least one apparatus monitoring vital patient data, such as patient monitoring devices 250.

Referring to FIG. 2, the vital patient data includes data from cardiac monitoring device 206 which provides electrocardiogram (EKG) monitoring data; patient pulse monitoring device 212; blood pressure monitoring device 222; pulmonary monitoring device 230 which provides respiratory data, and cerebral monitor 232 which provides electroencephalogram (EEG) monitoring data. Vital patient data may include manual monitoring of the patient emotional state 240 and manual monitoring of the patient physical state 242. The patient physical state may include trauma 244 or labor 246.

Step 402 includes the step of providing at least one processor 260 processing the vital patient data. Step 404 includes the step of the at least one processor 260 selecting at least one hypnotherapeutic treatment modality based on the processing of the vital patient data.

Following the processing of the vital patient data in Step 404, the processor initiates the at least one selected hypnotherapeutic treatment modality (Step 406); and evaluates whether the patient requires additional hypnotherapeutic treatment (Step 408). If NO, the processor ceases treatment (Step 410), and if YES, the processor evaluates whether the at least one selected hypnotherapeutical treatment requires adjusting (Step 412).

If NO, the processor continues treatment for a time period (Step 414) until again performing the step of evaluating whether the patient requires additional hypnotherapeutic treatment (Step 408). If YES, the processor evaluates whether frequency or time period of duration of the treatment is correct (Step 416).

If NO, the processor adjusts the frequency (Step 418) and continues treatment for a time period (Step 420) until again performing the step of evaluating whether the patient requires additional hypnotherapeutic treatment (Step 408). If YES, the processor evaluates whether the at least one selected treatment modality is correct (Step 422). If YES, the processor continues treatment for a time period (Step 424) until again performing the step of evaluating whether the patient requires additional hypnotherapeutic treatment (Step 408). If NO, the processor selects at least one different treatment (Step 426) and begins at least the at least one different treatment for a time period (Step 428) until again performing the step of evaluating whether the patient requires additional hypnotherapeutic treatment (Step 408).

As disclosed previously with respect to FIGS. 1-2, the processor 260 is operatively coupled to memory storage 264 for the hypnotherapeutical treatment modality, with the memory storage 264 storing at least one of a musical 266, auditory or lingual 268, visual 270 and olfactory treatment modality 272 or the combination treatment 288. The processor 260 may monitor the vital patient data by remote monitoring 254 over a network 252.

The foregoing embodiments of the present disclosure provide an interactive biological stabilization device, an interactive biological stabilization system, and an interactive biological stabilization method which combine medical science and clinical hypnotherapy. The purpose of the IBS system is to interactively induce and stabilize to the best possible health condition of a patient through clinical hypnotherapy by monitoring patient vital signs. The device is designed to be at the bedside of a patient in hospitals and medical centers and is able to respond to patient needs on a 24 hour basis.

The IBS system has interactive capabilities that serve the individual needs of each patient. The unit is programmed with custom made applications to cater to any pre- or post-operative situation in any medical specialty department. For instance, if the unit reads that a patient's blood pressure is rising above normal, the unit will tap a hypnotherapy application that will induce the body to lower its blood pressure to a stable, healthy condition. Because of the audible, personalized nature of the unit, no nurse or medical staff is needed immediately to aid the patient, since the IBS system provides immediate attention to the patient. The unit works interactively with the vital signs of each patient and delivers hypnotherapy applications accordingly.

Figure 5:
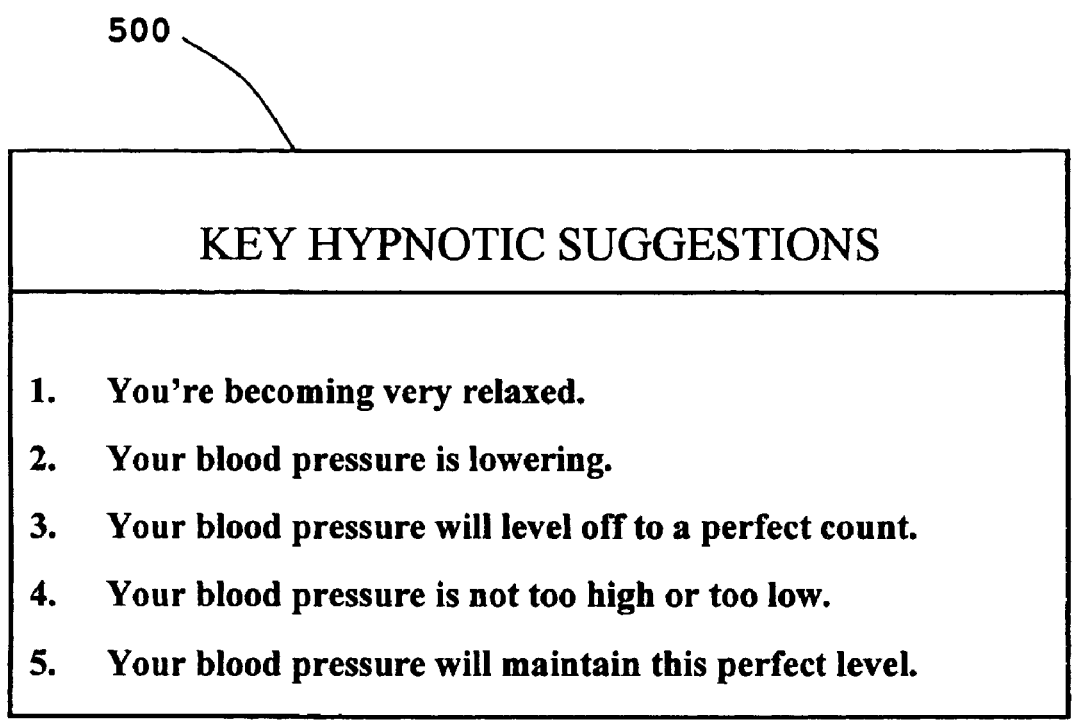
FIG. 5 is a diagram illustrating exemplary hypnotic suggestions according to the present disclosure.

As shown in FIG. 5, in the event that the IBS system 200 reads a patient's vital signs as indicating, for example and not limited to, high blood pressure (hypertension), the audio application 500 will automatically begin in order to stabilize his/her blood pressure. The audio messages which can be played are the following:

1. You're becoming very relaxed.
2. Your blood pressure is lowering.
3. Your blood pressure will level off to a perfect count.
4. Your blood pressure is not too high or too low.
5. Your blood pressure will maintain this perfect level.

The IBS system can also be set to a specific application manually by a doctor or nurse as they deem necessary. Whether a hypnotherapy application is administered manually or automatically, the unit acts interactively to monitor a patient's vital signs. In the event of an emergency condition, the IBS system is designed to emit an audible alarm to alert medical staff of danger and will immediately printout or display a reading of a patient's vital statistics. The computerized aspect of the IBS system reduces human error.

The hypnotherapeutic treatments may be applied to and specifically tailored for patient conditions, such as heart disease, hysteria, asthma or emphysema, labor or birth and post-operative or non-operative intensive care treatment, and panic and anxiety disorders.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. A method for interactively biologically stabilizing a patient, the method comprising the steps of:
    monitoring vital patient data;
    processing the vital patient data via at least one processor, the at least one processor configured for recognizing a distress condition and selecting at least one initial hypnotherapeutic treatment modality based on the processing of the vital patient data including the recognized distress condition;
    actively inducing a clinically hypnotic state in the patient by exposing the patient to at least one hypnotic suggestion wherein the at least one initial hypnotherapeutic treatment modality varies based upon the particular distress condition recognized; and
    initiating the at least one selected hypnotherapeutic treatment based on the recognition of the distress condition.

2. The method for interactively biologically stabilizing a patient according to claim 1, further comprising steps of:
    continuing monitoring the vital patient data; and
    wherein the at least one processor
    evaluates whether the patient requires additional hypnotherapeutic treatment using the vital patient data,
        wherein if the patient does not require additional treatment, the at least one processor ceases treatment, and
        wherein if the patient does require additional treatment, the at least one processor evaluates whether the at least one selected hypnotherapeutic treatment requires adjusting.

3. The method for interactively biologically stabilizing a patient according to claim 2, wherein the at least one processor, upon evaluating whether the at least one selected hypnotherapeutic treatment requires adjusting,
    if the at least one selected hypnotherapeutic treatment does not require adjusting, continues treatment for a time period until again performing the step of evaluating whether the patient requires additional hypnotherapeutic treatment; and
    if the at least one selected hypnotherapeutic treatment does require adjusting, evaluates whether frequency of the treatment is correct.

4. The method for interactively biologically stabilizing a patient according to claim 3, wherein the at least one processor, upon evaluating whether frequency of the treatment is correct,
    if the frequency of the treatment is not correct, adjusts the frequency and continues treatment for a time period until again performing the step of evaluating whether the patient requires additional hypnotherapeutic treatment; and
    if the frequency of the treatment is correct, evaluates whether the treatment modality is correct.

5. The method for interactively biologically stabilizing a patient according to claim 4, wherein the at least one processor, upon evaluating whether the at least one selected treatment modality is correct, and
    if the at least one selected treatment modality is correct, continues treatment for a time period until again performing the step of evaluating whether the patient requires additional hypnotherapeutic treatment; and
    wherein if the at least one selected treatment modality is not correct, selects at least one different treatment and begins at least the at least one different treatment for a time period until again performing the step of evaluating whether the patient requires additional hypnotherapeutic treatment.

6. The method for interactively biologically stabilizing a patient according to claim 1, wherein the at least one processor is operatively coupled to a memory storage for the hypnotherapeutic treatment modality, the memory storage storing at least one of a musical, auditory, lingual, visual, olfactory and combination treatment modality.

7. The method for interactively biologically stabilizing a patient according to claim 1, wherein the vital patient data is selected from the group consisting of pulse, blood pressure, electrocardiogram (EKG), pulmonary function, and electroencephalogram (EEG).

8. The method for interactively biologically stabilizing a patient according to claim 1, wherein the at least one processor monitors the vital patient data by remote monitoring over a network.

9. An interactive biological stabilization (IBS) device comprising:
at least one communication path enabling operative coupling with at least one patient data monitoring device; and
a processing device enabled for operative coupling with the at least one patient monitoring device through the at least one communication path and processing the patient data received from the at least one patient data monitoring device through the at least one communication path for recognizing a distress condition,
the processing device including:
a hypnotherapeutic treatment decision block selecting at least one initial hypnotherapeutic treatment modality based on the recognized distress condition associated with the patient data received from the at least one patient data monitoring device through the at least one communication path, wherein the at least one initial hypnotherapeutic treatment modality varies based upon the particular distress condition recognized, the at least one hypnotherapeutic treatment modality configured to actively induce a clinically hypnotic state in the patient via emission of at least one hypnotic suggestion.

10. The interactive biological stabilization (IBS) device according to claim 9, further comprising:
a hypnotherapeutic treatment memory storing therapeutic indications for at least one hypnotherapeutic treatment modality, the hypnotherapeutic treatment memory operatively coupled to the treatment decision block;
a hypnotherapeutic treatment selection interface operatively coupled to the hypnotherapeutic treatment decision block; and
a treatment initiation circuit operatively coupled to the treatment selection interface, the treatment initiation circuit initiating the at least one selected hypnotherapeutic treatment to a patient responsive to the recognition of the distress condition.

11. The IBS device according to claim 9, wherein the processing device further comprises:
a feedback loop operatively coupled to the at least one patient monitoring device and receiving patient data through the at least one communication path and operatively coupled to the treatment decision block; and
a time period modulation block operatively coupled to the feedback loop and to the treatment decision block, the time period modulation block adjusting the time period for the at least one selected hypnotherapeutic treatment modality upon receiving a signal from the treatment decision block and based on the feedback loop;
a treatment modality block operatively coupled to the feedback loop and to the treatment decision block, the treatment modality block selecting at least another one of the at least one hypnotherapeutic treatment modality upon receiving a signal from the treatment decision block and based on the feedback loop.

12. The IBS device according to claim 9, wherein the processing device further comprises:
a treatment termination block operatively coupled to the treatment decision block, the treatment termination block terminating the at least one selected hypnotherapeutic treatment modality upon receiving a signal from the treatment decision block.

13. The IBS device according to claim 9, wherein the hypnotherapeutic treatment modality is selected from the group consisting of a musical, auditory, lingual, visual, olfactory, and combination treatment modality.

14. The IBS device according to claim 9, wherein the patient data is selected from the group consisting of pulse, blood pressure, electrocardiogram (EKG), pulmonary function, and electroencephalogram (EEG).

15. A system for interactively biologically stabilizing a patient, the system comprising:
at least one patient data monitoring device; and
a processing device operatively coupled with the at least one patient monitoring device through at least one communication path for processing the patient data received from the at least one patient data monitoring device through the at least one communication path for recognizing a distress condition,
the processing device including:
a hypnotherapeutic treatment decision block for selecting at least one initial hypnotherapeutic treatment modality based on the recognized distress condition associated with the patient data received from the at least one patient data monitoring device through the at least one communication path, wherein the at least one initial hypnotherapeutic treatment modality varies based upon the particular distress condition recognized, the at least one hypnotherapeutic treatment modality configured to actively induce a clinically hypnotic state in the patient via emission of at least one hypnotic suggestion.

16. The system for interactively biologically stabilizing a patient according to claim 15, wherein the processing device further comprises:
a hypnotherapeutic treatment memory storing therapeutic indications for at least one hypnotherapeutic treatment modality, the hypnotherapeutic treatment memory operatively coupled to the treatment decision block;
a hypnotherapeutic treatment selection interface operatively coupled to the hypnotherapeutic treatment decision block; and
a treatment initiation circuit operatively coupled to the treatment selection interface, the treatment initiation circuit initiating the at least one selected hypnotherapeutic treatment to a patient responsive to the recognition of the distress condition.

17. The system for interactively biologically stabilizing a patient according to claim 15, wherein the processing device further comprises:
a feedback loop operatively coupled to the at least one patient monitoring device and receiving patient data through the at least one communication path and operatively coupled to the treatment decision block; and
a time period modulation block operatively coupled to the feedback loop and to the treatment decision block, the time period modulation block adjusting the time period for the at least one selected hypnotherapeutic treatment modality upon receiving a signal from the treatment decision block and based on the feedback loop;

a treatment modality block operatively coupled to the feedback loop and to the treatment decision block, the treatment modality block selecting at least another one of the at least one hypnotherapeutic treatment modality upon receiving a signal from the treatment decision block and based on the feedback loop.

18. The system for interactively biologically stabilizing a patient according to claim 15, wherein the processing device further comprises:

a treatment termination block operatively coupled to the treatment decision block, the treatment termination block terminating the at least one selected hypnotherapeutic treatment modality upon receiving a signal from the treatment decision block.

19. The system for interactively biologically stabilizing a patient according to claim 15, wherein the hypnotherapeutic treatment modality is selected from the group consisting of a musical, auditory, lingual, visual, olfactory and combination treatment modality.

20. The system for interactively biologically stabilizing a patient according to claim 15, wherein the patient data is selected from the group consisting of pulse, blood pressure, electrocardiogram (EKG), pulmonary function, and electroencephalogram (EEG).

* * * * *